(12) United States Patent
Ghassemzadeh et al.

(10) Patent No.: US 9,445,769 B2
(45) Date of Patent: Sep. 20, 2016

(54) METHOD AND APPARATUS FOR DETECTING DISEASE REGRESSION THROUGH NETWORK-BASED GAIT ANALYSIS

(71) Applicants: AT&T Intellectual Property I, L.P., Atlanta, GA (US); President and Fellows of Harvard College, Cambridge, MA (US)

(72) Inventors: Saeed S. Ghassemzadeh, Andover, NJ (US); Lusheng Ji, Randolph, NJ (US); Robert Raymond Miller, II, Convent Station, NJ (US); Manish Gupta, Cambridge, MA (US); Vahid Tarokh, Cambridge, MA (US)

(73) Assignees: President and Fellows of Harvard College, Cambridge, MA (US); AT&T Intellectual Property I, L.P., Atlanta, GA (US)

( * ) Notice: Subject to any disclaimer, the term of this patent is extended or adjusted under 35 U.S.C. 154(b) by 248 days.

(21) Appl. No.: 14/099,570

(22) Filed: Dec. 6, 2013

(65) Prior Publication Data
US 2015/0157274 A1   Jun. 11, 2015

(51) Int. Cl.
*G06N 99/00*   (2010.01)
*A61B 5/00*   (2006.01)
(Continued)

(52) U.S. Cl.
CPC ............ *A61B 5/7275* (2013.01); *A61B 5/112* (2013.01); *A61B 5/1123* (2013.01); *A61B 5/4082* (2013.01); *G06F 19/3418* (2013.01); *A43B 3/0005* (2013.01); *A61B 5/002* (2013.01);
(Continued)

(58) Field of Classification Search
None
See application file for complete search history.

(56) References Cited

U.S. PATENT DOCUMENTS 5,678,448 A   10/1997   Fullen et al.
5,955,667 A   9/1999   Fyfe
(Continued)

FOREIGN PATENT DOCUMENTS

EP   1464281 B1   10/2004
WO   WO 2004084725 A1   10/2004
(Continued)

OTHER PUBLICATIONS

Barth, J. et al. (2011). "Biometric and mobile gait analysis for early diagnosis and therapy monitoring in Parkinson's disease." Engineering in Medicine and Biology Society, EMBC, 2011 Annual International Conference of the IEEE. IEEE, 2011. DOI:10.1109/IEMBS.2011.6090226.*
(Continued)

*Primary Examiner* — Stanley K Hill
*Assistant Examiner* — Benjamin Buss (57) ABSTRACT

A method, computer-readable storage device and apparatus for determining a regression of a medical condition are disclosed. For example, a method receives characteristics of motion information, wherein the characteristics of motion information is based upon gait information, compares the characteristics of motion information over a time period to a profile of the medical condition, wherein the profile of the medical condition comprises a plurality of signatures associated with different stages of the medical condition, determines a potential presence of the regression of the medical condition when the characteristics of motion information matches one of the plurality of signatures, and transmits a notification of the potential presence of the regression of the medical condition.

20 Claims, 3 Drawing Sheets

(51) Int. Cl.
*A61B 5/11* (2006.01)
*G06F 19/00* (2011.01)
*A43B 3/00* (2006.01)

(52) U.S. Cl.
CPC .............. *A61B5/0022* (2013.01); *A61B 5/1117* (2013.01); *A61B 5/1126* (2013.01); *A61B 5/4878* (2013.01); *A61B 5/6802* (2013.01); *A61B 5/6829* (2013.01); *A61B 5/7267* (2013.01); *A61B 5/7405* (2013.01); *A61B 2562/0219* (2013.01); *A61B 2562/0247* (2013.01)

(56) References Cited

U.S. PATENT DOCUMENTS

| | | | |
|---|---|---|---|
| 6,360,597 B1 | 3/2002 | Hubbard | |
| 2006/0252999 A1 | 11/2006 | Devaul et al. | |
| 2007/0173903 A1* | 7/2007 | Goren | A61N 1/32 607/49 |
| 2007/0263907 A1* | 11/2007 | McMakin | G01S 13/887 382/115 |
| 2008/0045804 A1* | 2/2008 | Williams | A61B 5/112 600/300 |
| 2008/0053253 A1 | 3/2008 | Moore et al. | |
| 2008/0214360 A1* | 9/2008 | Stirling | A61B 5/1038 482/9 |
| 2009/0216156 A1 | 8/2009 | Lengsfeld et al. | |
| 2009/0247910 A1 | 10/2009 | Klapper | |
| 2010/0169409 A1* | 7/2010 | Fallon | G06F 19/345 709/203 |
| 2011/0092860 A1* | 4/2011 | Salarian | A61B 5/4023 600/595 |
| 2011/0218463 A1 | 9/2011 | Hodgins et al. | |
| 2012/0253234 A1* | 10/2012 | Yang | A61B 5/1038 600/595 |
| 2013/0041290 A1 | 2/2013 | Kording et al. | |
| 2013/0123665 A1 | 5/2013 | Mariani et al. | |
| 2013/0165820 A1* | 6/2013 | Lin | A61B 5/1038 600/595 |
| 2013/0253334 A1* | 9/2013 | Al-Ali | A61B 5/002 600/476 |
| 2014/0162933 A1* | 6/2014 | Hatchwell | C12Q 1/6883 514/1.1 |
| 2014/0257047 A1* | 9/2014 | Sillay | A61B 5/11 600/301 |
| 2015/0213729 A1* | 7/2015 | Rhea | G06F 19/3481 434/247 |

FOREIGN PATENT DOCUMENTS

| | | |
|---|---|---|
| WO | WO 2012167328 A1 | 12/2012 |
| WO | WO 2013038214 A2 | 3/2013 |
| WO | WO 2013054258 A1 | 4/2013 |

OTHER PUBLICATIONS

Lara, O.D. et al. (2013). "A survey on human activity recognition using wearable sensors." Communications Surveys & Tutorials, IEEE 15.3: 1192-1209. Date of original publication: Nov. 29, 2012. DOI:10.1109/SURV.2012.110112.00192.*

Li, S. et al. (2011). "A novel gait recognition analysis system based on body sensor networks for patients with parkinson's disease." International Journal of Communication Networks and Distributed Systems 7.3-4: 262-274. DOI:10.1109/GLOCOMW.2010.5700321.*

Lakany, H. (2008). "Extracting a diagnostic gait signature." Pattern recognition 41.5: 1627-1637. DOI: doi:10.1016/j.patcog.2007.11.004.*

Tripoliti, E.E. et al. (Apr. 2013). "Automatic detection of freezing of gait events in patients with Parkinson's disease." Computer methods and programs in biomedicine 110.1: 12-26. doi:10.1016/j.cmpb.2012.10.016.*

Moore, Steven T., Hamish G. MacDougall, and William G. Ondo. "Ambulatory monitoring of freezing of gait in Parkinson's disease." Journal of neuroscience methods 167.2 (2008): 340-348. http://www.psych.usyd.edu.au/staff/hamish/Publications/081113_4.pdf.

Han, Jonghee, et al. "Gait detection from three dimensional acceleration signals of ankles for the patients with Parkinson's disease." IEEE the International Special Topic Conference on Information Technology in Biomedicine, Ioannina, Epirus, Greece, 2006. http://medlab.cs.uoi.gr/itab2006/proceedings/biosignal%20analysis/108.pdf.

Salarian, Arash, et al. "Gait assessment in Parkinson's disease: toward an ambulatory system for long-term monitoring." Biomedical Engineering, IEEE Transactions on 51.8 (2004): 1434-1443. http://www.cse.ohio-state.edu/~prasun/research/gait/SalarianA_DBSgait.pdf.

Morris, Stacy J., and Joseph a. Paradiso. "A compact wearable sensor package for clinical gait monitoring." Motorola Journal (2002): 7-15. http://resenv.media.mit.edu/pubs/papers/2002-12-SIGSS-Offspring.pdf.

Morris, Stacy J. "A shoe-integrated sensor system for wireless gait analysis and real-time therapeutic feedback." Diss. Massachusetts Institute of Technology, 2004, Partial Contents: Title Page, Abstract, Table of Contents, Chapter, Sections 1.1-1.5 (Introduction), full certified document consists of 314 pages and can be retrieved at: http://resenv.media.mit.edu/pubs/theses/sjmorrisSCDthesis.pdf.

* cited by examiner

METHOD AND APPARATUS FOR DETECTING DISEASE REGRESSION THROUGH NETWORK-BASED GAIT ANALYSIS

BACKGROUND

Pedometers are popular for use as everyday exercise accessories. Often worn on the belt, pedometers can record the number of steps that a user has walked, and thus the distance. Pedometers, or step counters, can provide encouragement to a user to compete with oneself in getting fit and losing weight. However, most pedometers do not have the ability to record and store data. In addition, such pedometers often erroneously record movements other than walking, such as bending to tie shoes, or a road bump while travelling in a vehicle. At the same time, falls are serious hazards for older individuals as coordination, muscle strength, and balance tend to deteriorate with age and advance of chronic diseases such as Parkinson's disease and the like. In managed care as well as home settings, injuries resulting from falls may render older individuals incapable of calling for help and/or requiring emergency treatment. Resulting bone fractures can require lengthy and costly treatment, severely impact quality of life, and can trigger a cascade of other factors that lead to a rapid decline of the health of an individual.

SUMMARY

In one embodiment, the present disclosure provides a method, computer-readable storage device, and apparatus for determining a regression of a medical condition. For example, a method receives characteristics of motion information, wherein the characteristics of motion information is based upon gait information, compares the characteristics of motion information over a time period to a profile of the medical condition, wherein the profile of the medical condition comprises a plurality of signatures associated with different stages of the medical condition, determines a potential presence of the regression of the medical condition when the characteristics of motion information matches one of the plurality of signatures, and transmits a notification of the potential presence of the regression of the medical condition.

BRIEF DESCRIPTION OF THE DRAWINGS

The present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present disclosure relates generally to tracking of physical activities and, more particularly, to a method, computer-readable storage device, and apparatus for determining a medical condition regression based upon analysis of gait information. For example, in one embodiment different characteristics of human motion are detected through an analysis of a user's gait. The user's gait information can be gathered from multiple sensors in the soles of the shoes of the user, collected and sent to a network-based monitoring server to perform gait analysis. In one embodiment, a training data set from a plurality of users is used to create "signatures" for different movements associated with different medical conditions, e.g., degenerative diseases, and more particularly different stages within these diseases. For example, a user with Parkinson's disease may exhibit different movement patterns than those of users who do not suffer from the disease or a similar condition. In addition, different stages of Parkinson's disease may be associated with different patterns of walking, shuffling, loss of balance, stride lengths, activity levels, and so forth. Thus, when analyzing the gait information from a user, characteristics of motion information can be determined from the raw gait information and compared to different signatures to determine whether a user is exhibiting a movement pattern that matches a particular disease and/or a particular stage of such a disease. A user profile may also be created to store user parameters, such as age and weight, and to track a user's medical condition regression over time. These measurements can also be used to indicate foot abnormalities, such as faulty pressure distribution, which can be discovered and ameliorated by proper application of orthoses.

Figure 1:
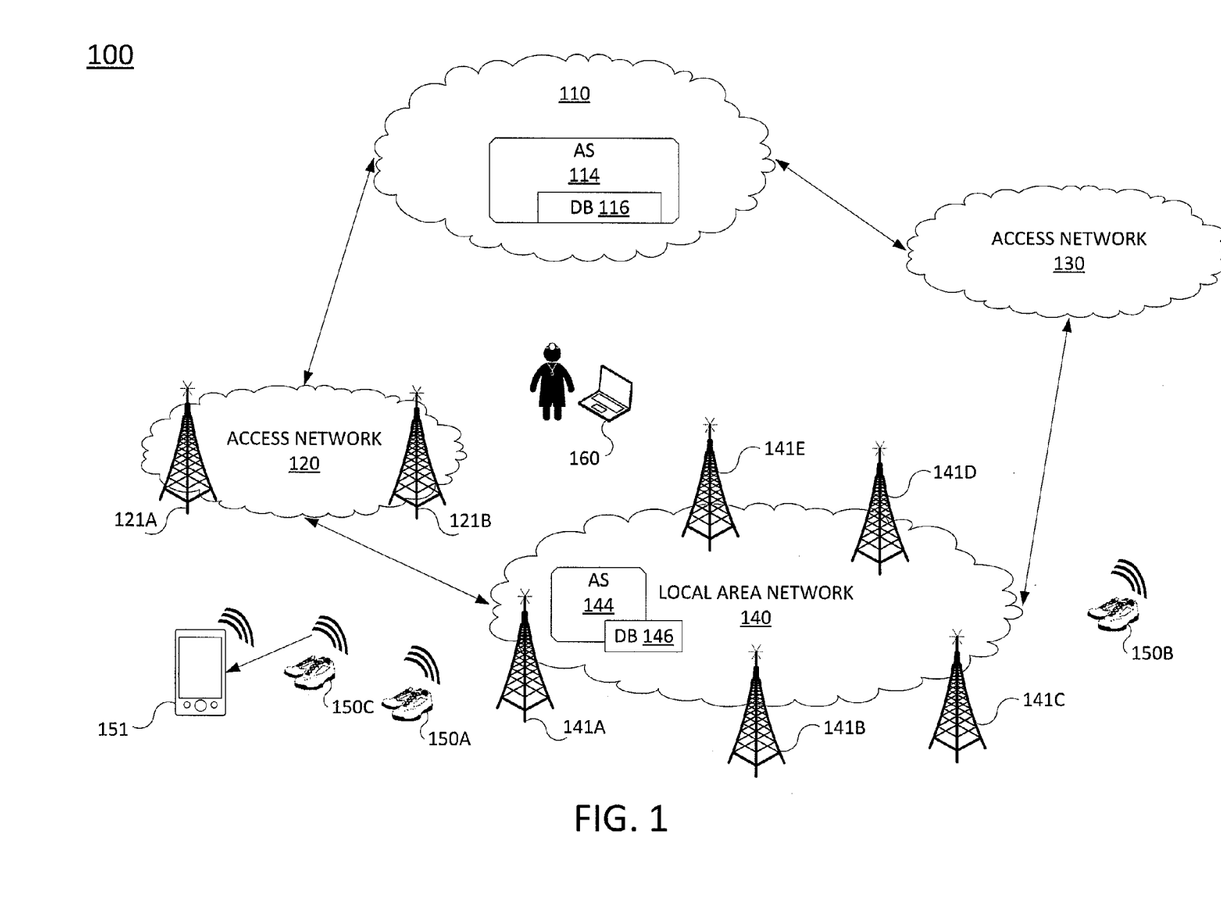
FIG. 1 illustrates one example of a communication network of the present disclosure.

To aid in understanding the present disclosure, FIG. 1 is a block diagram depicting one example of a communication network 100 suitable for use in performing or enabling some or all of the features described herein. The communication network 100 may be any type of communication network, such as for example, a traditional circuit switched network (e.g., a public switched telephone network (PSTN)) or a packet network such as an Internet Protocol (IP) network (e.g., an IP Multimedia Subsystem (IMS) network), an asynchronous transfer mode (ATM) network, a wireless network, a cellular network (e.g., 2G, 3G, and the like), a long term evolution (LTE) network, and the like related to the current disclosure. It should be noted that an IP network is broadly defined as a network that uses Internet Protocol to exchange data packets.

In one embodiment, the network 100 may comprise a core network 110. The core network 110 may be in communication with one or more access networks 120 and 130. For instance, access network 120 may comprise a wireless access network (e.g., an IEEE 802.11/Wi-Fi network, a wide area network (WAN) and the like) or a cellular access network. Thus, in one example, access network 120 may include one or more wireless transceivers 121A and 121B, which may alternatively comprise cellular base stations, base transceiver stations (BTSs), NodeBs, evolved NodeB's (eNodeBs), wireless access points, and so forth. Similarly, access network 130 may comprise a wired access network such as a circuit switched access network, a cable access network, a digital subscriber line (DSL) access network, and so forth. The core network 110 and the access networks 120 and 130 may be operated by different service providers, the same service provider or a combination thereof.

In one embodiment, network 100 also includes a local area network (LAN) 140. For example, local area network 140 may comprise a wireless local area network (LAN), a Bluetooth network, a ZigBee network, and so forth. For instance, local area network 140 may be a home network or an office network, e.g., a network that is maintained by a hospital, an elder care facility, a rehabilitation center, and so forth. As illustrated, local area network 140 may comprise a coverage network or mesh network of ZigBee access points 141A-141E which may be connected to one another and to other devices and networks via an Ethernet network. However, it should be noted that ZigBee is designed for static end nodes. Thus, local area network 140 may comprise a ZigBee mesh network modified to enable handoffs between the different ZigBee access points 141A-141E.

In one example, the ZigBee access points 141A-141E are in communication with one or more sets of wearable devices 150A-150C. Each of the sets of wearable devices 150A-150C may comprise a pair of "smart" shoes, or shoe inserts. The term "smart" implies ability to measure, record, process, and communicate information. In addition, each of the sets of wearable devices 150A-150C may include one or more components for collecting gait information of a user, such as sole pressure sensors, accelerometers and gyroscopes. The wearable devices may also include notification means, such as an audio alarm, to warn a user of danger (e.g. unstable gait that could result in a proximate fall). In one example, each of the sets of wearable devices 150A-150C comprises a respective component for each foot of a user. However, in another example it may be sufficient to have a single wearable device for only one foot of a user. Notably, the users, and hence the sets of wearable devices 150A-150C, may move throughout the coverage area of local area network 140, thus benefiting from the ability of handing off between the ZigBee access points 141A-141E.

Figure 3:
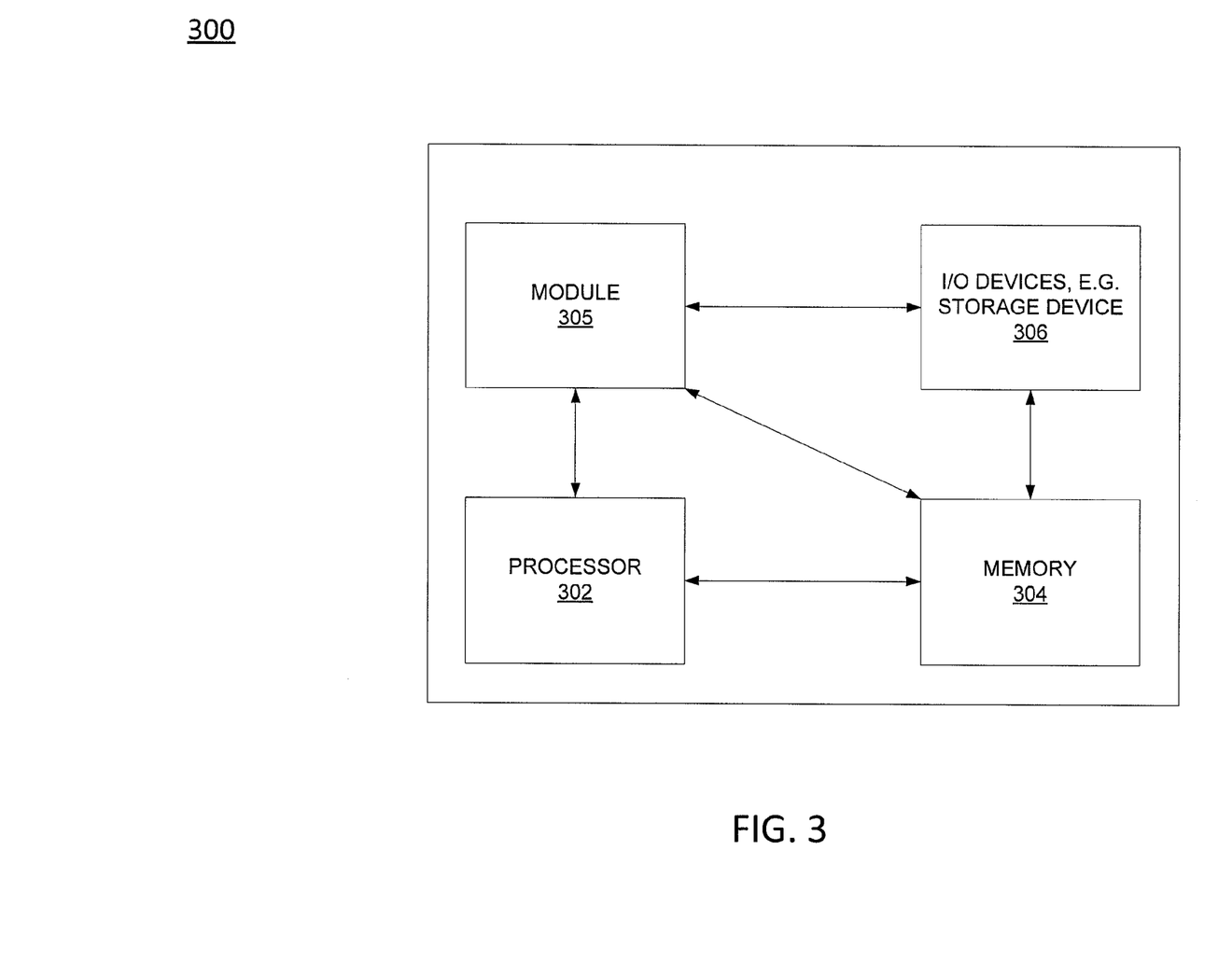
FIG. 3 illustrates a high-level block diagram of a general-purpose computer suitable for use in performing the functions described herein.

In one embodiment, the core network 110 may include an application server (AS) 114 and a database (DB) 116. Notably, AS 114 may perform some or all of the functions described herein in connection with determining a medical condition regression. For example, AS 114 may collect and store in database 116 user gait information received from the one or more sets of wearable devices 150A-150C. Database 116 may also store user profiles, generic signatures for different modes of motion or types of activities, disease/medical condition profiles, including signatures for different stages of one or more diseases, and so forth. In one embodiment, gait information may be forwarded from local area network 140 via access network 120 and/or access network 130 to AS 114. At AS 114, the gait information may be collected, stored in database 116 and used for determining a medical condition regression. In one embodiment, the AS 114 may comprise a general purpose computer as illustrated in FIG. 3 and discussed below. Notably, AS 114 is suitable for performing some or all of the functions of the present disclosure for determining a medical condition regression as described in greater detail below. In addition, although only a single AS 114 and a single DB 116 are illustrated in core network 110, it should be noted that any number of application servers 114 or databases 116 may be deployed.

In one embodiment, the gait information includes information which identifies a particular wearable device or set of wearable devices as a source of the gait information. The gait information may also include pressure information, acceleration information (including both linear and rotational accelerations), gyroscopic information, elevation information, time information and/or location information. In particular, raw gait information, such as pressure information, acceleration information, gyroscopic information, elevation information, temperature and fluid content (edema) may be collected from the various sensors of a wearable device. Other components may also contribute to the gait information prior to the gait information reaching AS 114. For example, each of the ZigBee access points 141A-141E may time stamp any gait information that is received from one of the sets of wearable devices 150A-150C. In addition, in one example the ZigBee access points 141A-141E may also append their location information to any gait information that is received. In another example, each ZigBee access point 141A-141E may simply append its own identity to any gait information that is received, where the identity information is sufficient to indicate the approximate location of the user relative to a corresponding ZigBee access point.

In one embodiment, AS 114 may also determine characteristics of motion information from the gait information. For example, AS 114 may gather gait information relating to a user over a period of time, e.g., over an hour, over a day, over a week, and so forth. From the gait information, AS 114 may then determine characteristics of motion such as a stride length, a speed, an acceleration, an elevation, and so forth, as well as different modes of motion or different types of activities that a user has engaged in at various times within the time period. For example, accelerometers within one of the sets of wearable devices 150A-150C may indicate accelerations along different axes. Accordingly, the raw gait information may simply include an acceleration and an indication of which component recorded the acceleration. Different accelerations may then be vector summed by AS 114 to derive an overall acceleration magnitude and direction which may then be included as part of the characteristics of motion information.

As another example, to determine a mode of motion for any particular time within the time period, AS 114 may compare the gait information and/or characteristics of motion information to known signatures for different common modes of motion that are stored in database 116. Exemplary modes of motion may broadly include postures, stances, movement patterns and/or types of activities such as: running, walking, falling, jumping, standing, cycling, sitting, shuffling, and lying down and so forth. It should be noted that "running" may optionally be further defined with more granularity such as speed walking, jogging, sprinting, and the like. For instance, a running signature may indicate a sequence of: a strong pressure on the left foot, acceleration of the right foot, a strong force and deceleration of the right foot, acceleration of the left foot, and so forth. On the other hand, a walking signature may be similar to the running signature, but the forces and accelerations observed may be of lesser magnitude than the signature for running. Similarly, a standing signature may comprise steady and balanced pressures on both feet (with zero acceleration).

Notably, in the context of the present disclosure, exemplary modes of motion may also include different movement patterns that are associated with regressive diseases and/or stages within the regressive diseases. Taking Parkinson's disease as an example, this disease is commonly characterized by five stages as described by Hoehn and Yahr:

Stage 0—No signs of disease;
Stage 1—Symptoms on one side of the body only;
Stage 2—Symptoms on both sides of the body; no impairment of balance;
Stage 3—Balance impairment; mild to moderate disease; physically independent;
Stage 4—Severe disability; still able to walk or stand unassisted; and
Stage 5—Wheelchair bound or bedridden unless assisted.

Some of the symptoms associated with Parkinson's disease include:
Tremor at rest—shaking, most often seen in the hands;
Rigidity—stiffness of the muscles on passive movement;

Bradykinesia—slowness of movements (including akinesia, lack of movement, and hypokinesia, reduced amplitude of movements);

Postural instability—difficulty with balance.

These symptoms may manifest themselves to varying degrees depending upon the stage of disease. However, a user with Parkinson's disease that is exhibiting symptoms will have gait information that will reveal tremors or other movements that would not be present if the user did not suffer from Parkinson's disease and/or did not have such symptoms. Thus, AS 114 may store signatures for "normal" standing, standing with Parkinson's symptoms of stage 2, standing with Parkinson's symptoms of stage 3, standing with Parkinson's symptoms of stage 4, and so forth. Similarly, AS 114 may store signatures for other modes of motion that are "normal" as well as specific to other diseases, and stages within such diseases, e.g., "normal" walking, walking with Parkinson's symptoms of stage 1, walking with Parkinson's symptoms of stage 2, walking with Parkinson's symptoms of stage 3, sitting with Huntington disease of an early stage, and so on.

It should be noted that various progressive diseases have clinically accepted stages with various criteria indicative of the different stages. However, embodiments of the present disclosure do not require prior knowledge of the indicia of each stage. In other words, it is not necessary for the connection between the raw gait information and Parkinson's disease staging to be apparent to the observer. For example, in one embodiment, training data is generated from test subjects performing common motions, stances and/or postures, e.g., running, jumping, standing, sitting, walking, falling, cycling, lying down, etc. In addition, in the context of the present disclosure, different test subjects that are diagnosed as having a particular disease and/or a stage within such a disease may be used to generate at least a portion of the test data. Thereafter, a signature for different modes of motion that are specific to a particular disease and/or a particular disease stage can be generated. Thus, a disease profile may include a plurality of signatures for different modes of motion as exemplified at different stages of the disease.

For example, in one embodiment, each mode of motion can be modeled as a Hidden Markov Model (HMM). For example, a subset of the training data may be used to determine "principal components" associated with different stages of each of the modes of motion, which are the "hidden states" of the HMM. A subset of the training data is also used to determine emission probabilities and transition probabilities between the stages (i.e., between the hidden states). Thus, each HMM may comprise a signature which uniquely identifies one of the different modes of motion. Thereafter, AS 114 may statistically infer a best matching signature/HMM as compared to the observed gait information. In other words, AS 114 assumes the current mode of motion is the one having the HMM that best predicts the currently observed gait information. Illustrative examples of various algorithms for determining different modes of motion, or activity types, can be found in co-pending U.S. patent application Ser. No. 14/099,499, titled "METHOD AND APPARATUS FOR DETECTING MODE OF MOTION WITH PRINCIPAL COMPONENT ANALYSIS AND HIDDEN MARKOV MODEL", filed on the same date herewith and which is incorporated by reference herein in its entirety. However, any other methods of determining modes of motion, or activity types can be used by the present method.

As a further illustration, Parkinson's disease stage 3 (on the Hoehn and Yahr scale) is associated with slowing of body movements and some impairment of balance. Stage 4 is more strongly associated with rigidity and bradykinesia. Thus, a walking signature for stage 3 of the Parkinson's disease may reflect aspects of the gait that involve some inconsistencies between the left and the right foot (as exhibited by the gait information from the sensors on the respective feet). However, a walking signature for stage 4 of the Parkinson's disease may exhibit an even greater variation in gait information from the sensors on the respective feet, e.g., due to greater imbalance, as well as a different pressure pattern than that of stage 3, e.g., due to rigidity of movement. In still another example, an average stage 3 Parkinson's test subject may exhibit otherwise "normal" walking for 90% of the time, while for 10% of the time, the average stage 3 Parkinson's test subject may exhibit walking that reflects a medical episode, e.g., akinesia. Accordingly, in one embodiment a "signature" for walking for stage 3 of the Parkinson's disease may account for the relative percentage of the time that a user may engage in "normal" walking versus an percentage of the time that the user exhibits other movements while attempting to walk, e.g., akinesia, bradykinesia, stumbles, falls, etc. However, in another embodiment, "walking" may have a first signature, while "akinesia", "bradykinesia" and other gait aspects that are indicative of a medical issue may each have their own separate and unique signatures.

Other characteristics of motion, such as speed and stride length, may also be determined from gait information in various ways. For instance, in one embodiment, global positioning system (GPS) location data is included in or appended to the gait information to allow a change in position over time to be determined. In this way, the average speed and speed at various times may be calculated. In addition, if the mode of motion is determined to be running or walking, the distance traveled in a particular time divided by a number of stances, e.g., steps, observed in the same time will indicate the average stride length. In another embodiment, one or more of the sets of wearable devices 150A-150C may include a pair of sensors, one for each foot, to determine a distance between the sensors. For example, the sensors can send and measure a round-trip time between the sensors, e.g., using infrared signals, radio frequency (RF) signals, acoustic signals, and the like to estimate a distance between the sensors.

In another embodiment, GPS location data may be unavailable. Accordingly, the gait information may include position information derived from one or more other sources. For instance, each of the ZigBee access points 141A-141E may append its identity and/or location information to any gait information that the ZigBee access point receives and forwards, thereby allowing AS 114 to determine the approximate location of a user at different times. For example, at a first time, gait information for the set of wearable devices 150A may be received and appended with the identity and/or location of ZigBee access point 141A. At a later time, gait information may be received for the same set of wearable devices 150A from ZigBee access point 141B. Thus, AS 114 can determine the approximate distance traveled, speed and so forth, based upon the difference in positions of the respective ZigBee access points.

Once various characteristics of motion are determined (including a number of different modes of motion the user has engaged in during a given time period), AS 114 may then determine whether or not a disease stage is reflected within the gait information/characteristics of motion information and/or whether a medical condition regression is exhibited (broadly the potential presence of a regression of a medical condition). For example, as mentioned above each stage of a disease may have its own signature, or plurality of signatures, which account for typical gait features associated with the disease stage. For instance, the average user with stage 3 Parkinson's may exhibit a different walk signature than a user with stage 4 Parkinson's, or a user without Parkinson's or similar disease/condition. Alternatively, or in addition, an average user with stage 3 Parkinson's may exhibit a normal walk for a certain percentage of the time (e.g., 90% of the time) and may exhibit specific instances that are indicative of Parkinson's symptoms, such as ankinesia, and bradykinesia, stumbling, falling and the like, for some of the time (e.g., 10% of the time). However, an average user with stage 4 Parkinson's may walk normally for 70% of the time and exhibit movements indicative of Parkinson's symptoms for 30% of the time, when walking. Thus, the "profile" for Parkinson's disease may include signatures for various modes of motion associated with different stages of the disease.

In one embodiment, database 116 stores a user profile which stores biometric information regarding a user and which tracks a user over multiple time periods. For instance, the user profile may store the age, weight, height, metabolic rate and so forth for the user. The user profile may also store data regarding the prior activity levels of the user in terms of stride length, distances traveled, speed of walking, running, cycling, etc., calories burned, and so forth. The user profile may further store data regarding previous determinations of the user as being associated with a particular disease stage. For example, AS 114 may have previously determined that a user's gait information was indicative of walking that fit a stage 2 Parkinson's walking signature. Alternatively, in one embodiment, the early stage of a disease can be determined by a physician for a user and AS 114 is simply tasked with monitoring the user's gait information to detect disease regression. A record of the prior determination may thus be stored in the user profile in database 116. Thereafter, during a later time period, AS 114 may determine that the user's gait information is reflective of walking that is best matched by the signature for stage 3 Parkinson's walking. Accordingly, in another example, AS 114 may determine a disease regression when there is a change in a disease stage categorization with respect to at least one mode of motion/type of activity.

Continuing the above example, while one data point now suggests that the user has progressed to stage 3, one or more other aspects of the characteristics of motion information may indicate that the user continues to be at stage 2. For instance, the user may continue to exercise on a regular basis and the gait information from the user's standing posture still indicates that the user still does not have significant balance issues. Nevertheless, AS 114 may determine that a disease regression is occurring where the user is beginning to exhibit signs of moving to the next stage of the disease progression in at least one aspect of the characteristics of motion.

It should be noted that in some cases, certain characteristics of motion, such as stride length, may be accounted for within the signature for a mode of motion at a particular disease stage. However, in another example, each of these additional characteristics of motion, such as stride length while walking, running, jogging, etc., an activity level, such as number of calories burned, speed while running or jogging, distance traveled, and so forth, may have its own signature that is associated with a disease stage. For example, database 116 may have a lookup table that correlates user parameters, such as sex, age and weight, with characteristics of motion information, such as an activity level to predict a disease stage. The lookup table may be populated by using the same test data from the same test subjects that belong to a particular disease category and/or stage. To illustrate, a user profile may store data that reflects an average stride length of the user when jogging. In addition, the user profile may also note that the user has been previously categorized as Parkinson's stage 2, e.g., based upon the observations of AS 114 at one or more earlier time periods. However, at a later time period, the characteristics of motion information may reflect a severely shortened stride length when the user is jogging. In this case, AS 114 may determine a disease regression based upon the change in stride length.

In one embodiment, it is sufficient to categorize a user as being associated with a particular disease stage based upon observing that the gait information for only one mode of motion/type of activity, e.g., walking, matches one of the various signatures contained within the disease profile. However, In an additional example, a disease regression may be determined by AS 114 only when at least two, or other threshold number of aspects of the characteristics of motion information match a respective signature associated with a disease stage. For instance, a user may match a signature for Parkinson's stage 3 walking. The user may also have a stride length that is categorized as Parkinson's stage 3, e.g., based upon the lookup table. Thus, in this case a disease regression may then be determined.

In one embodiment, AS 114 observes gait information of a user over a sufficient length of time before making a determination whether or not a disease regression is observed. For example, a user with no signs of Parkinson's disease and no family history may nevertheless be monitored for gait analysis in accordance with the present disclosure. If the user hurts his or her foot in an accident, the user may temporarily walk with a short and imbalanced gait. However, several hours later the user may resume a normal gait once the pain has subsided. Depending upon the signatures for various diseases/disease stages that may be generated, it is possible that the user's observed gait information may be mistaken for a pattern of an early stage of Parkinson's disease, e.g., if only the gait information from immediately after the accident is used. However, over the course of the entire day, or over several days, the observed gait information for "walking" may, on average, simply be "normal walking". Thus, in general, the present disclosure does not overweigh stand-alone short term events such as falling, tripping, or stumbling that are associated with temporary incidents. In other words, the monitoring time periods must be of a sufficient length so that false positives can be minimized.

However, in the aggregate, over a sufficient time period, such events may be reflective of disease regression. For example, a user who walks normally most of the time but who has balance issues may stumble more often that a user who does not have balance issues. Furthermore, the balance issues may have some relation to one or more stages of a regressive disease, such as stage 2 Parkinson's, stage 3 Parkinson's and so forth. For instance, over the course of an entire day the number of stumbling incidents of an average stage 2 Parkinson's sufferer while walking may be reflected in the signature/HMM for stage 2 Parkinson's walking. Thus, a user who is being observed by AS 114 may "match" this signature if the number of stumbles while walking causes the characteristics of motion information to be best fitted by the signature.

When AS 114 determines a disease regression, or a potential disease regression, AS 114 may also transmit a notification to one or more parties. For example, AS 114 may notify the user, a doctor, a nurse, a physical therapist and so forth, when the determination is made. For example, AS 114 may transmit a notification by email, text message, automated voice call or other methods of communications, e.g., to an endpoint device 160 of a doctor. In one embodiment, the notification may indicate the specific type of characteristic of motion information for which the regression is determined. For example, the notification may be sent to a doctor stating: "User is exhibiting walking patterns indicative of stage 3 Parkinson's disease. User was previously observed to be stage 2" or "User is exhibiting walking patterns indicative of stage 3 Parkinson's disease. User walking pattern was previously observed to be stage 2". It should be noted that a determination of disease/medical condition regression may be inaccurate in some cases. For instance, a user may not actually have progressed from stage 2 to stage 3 of the Parkinson's disease, but instead is due to the fact that user may have failed to take his/her medication, thereby leading to signs of stage 3 Parkinson's as reflected in the gait information/characteristics of motion information. Nevertheless, a notification to the user or other appropriate entities is still valuable because it may trigger an action to be taken for determining the actual cause of the change in gait information/characteristics of motion information.

In one embodiment, AS 114 may further suggest or trigger an intervention based upon the determination of a disease regression. For example, AS 114 may transmit the notification of the disease regression to a medical provider along with a recommendation as to where to find the user. For example, the user may be a patient in an elder care facility that is covered by local area network 140. Thus, the notification may include current location information of the user to assist a nurse or other caregiver in tracking down the patient within the facility in order to determine whether the patient has taken his or her prescription or whether there is truly a regression to a next stage of a disease.

In some cases, it may be helpful to know beforehand that a user has been diagnosed with a particular medical condition/disease. This enables AS 114 to more easily track the regression of the medical condition over time since AS 114 may only consider signatures within the profile of that particular medical condition. However, the present disclosure is not limited to detecting regression of a single medical condition, e.g., Parkinson's disease, but is applicable to various different types of regressive diseases/conditions including but not limited to: muscular dystrophy, multiple sclerosis, Alzheimer disease, Huntington disease, adrenoleukodystrophy, ataxia, dystonia, multiple system atrophy, arthritis (including osteoarthritis and rheumatoid arthritis), dementia and similar diseases and/or conditions that are associated with altered gait. Thus, in one embodiment, database 116 may store different medical condition profiles, each profile including various signatures associated with different stages of one of several medical conditions. Accordingly, AS 114 may distinguish among different types of diseases/medical conditions as well as stages with such diseases by matching observed gait information/characteristics of motion information to the best-fit signature.

Note that in some cases there may be similar gait symptoms associated with different diseases. Thus, in one embodiment, AS may transmit a notification of disease regression that reflects a first best match to a disease/disease stage and a second best match. For instance, the user's gait information may be a best match to an early stage Huntington disease but may also be a reasonable match to an early stage of Parkinson's disease. Thus, a notification that reflects both the first and second best matches may assist the user and/or a medical provider in exploring alternative plausible diagnoses.

The foregoing describes various functions of AS 114 (and database 116) in connection with embodiments of the present disclosure for determining a medical condition regression. However, it should be noted that in one example, local area network 140 may also include an application server (AS) 144 and a database 146 which may perform the same or similar functions to those of AS 114 in core network 110. In other words, AS 144 may also collect and store user gait information from the one or more sets of wearable devices 150A-150C via the ZigBee access points 141A-141E. Database 146 may also store user profiles, instructions relating to the tracking of different users, mode of motion signatures, disease profiles, and so forth to allow AS 144 to determine characteristics of motion information and/or to detect a medical condition regression. In one embodiment local area network 140 also provides access for endpoint device 160, e.g., a personal computer, a laptop computer, tablet computer, smart phone, and the like to connect to AS 144 and/or AS 114. For example, a doctor, a nurse, a technician, a patient, and so forth may use endpoint device 160 to access AS 114 and/or AS 144. In one embodiment, endpoint device 160 is connected directly to local area network 140. However, in another embodiment, endpoint device may be a remote device that connects to local area network 140 and AS 144 via one or more of access network 120, access network 130 and or core network 110.

In one example, one or more of the set of wearable devices, e.g., set 150C, may also communicate with a cellular base station 121A and/or 121B of access network 120 to upload gait information to a server performing functions for determining a medical condition regression. For example, the set of wearable devices 150C may include a subscriber identity module (SIM) card, a cellular antenna and/or any other components that may be required to enable cellular communications via access network 120. Alternatively, or in addition, the set of wearable devices 150C may communicate with access network 120 via cellular device 151. For example, cellular device 151 may comprise an intermediary unit, such as a cell phone, a personal base station, a femtocell or the like, for providing a tethering function to the set of wearable devices 150C. In other words, the set of wearable device 150C and the cellular device 151 may communicate using various cellular communication standards or using near field communication techniques such as Wi-Fi/IEEE 802.11, Bluetooth, ZigBee and so forth. Regardless of the specific technology or communication techniques used, access network 120 may thus receive gait information from the set of wearable devices 150C and forward such information to a server performing functions for determining a medical condition regression of the present disclosure.

In one example, the gait information is uploaded to AS 114 in the core network 110. However, in another example, the gait information may be passed to AS 144 in the local area network 140. For example, in one embodiment gait information of a user may still be managed via AS 144 in the local area network 140 when the user is not currently proximate to the local area network 140 and/or is not within range to communicate directly with components of local network 140.

In one embodiment, local area network 140 may comprise an indoor network, e.g., a combination of wired and wireless LANs within a user's home or of a medical facility such as a hospital, a rehabilitation center, an elder care facility, and the like. Thus, local area network 140 and access network 120 may be complimentary to one another, with local area network 140 providing the capability of uploading gait information while a user is indoors, and with the access network 120, e.g., a cellular network, providing coverage while the user is outdoors and/or while the user is outside of the communication range of the local area network 140.

In one embodiment, each of the sets of wearable devices 150A-150C may be configured to connect to local area network 140 and the ZigBee access points 141A-141E when available, and to connect to access network 120 only when local area network 140 is not available. In one example, when connecting to access network 120, the cellular device 151 may time stamp gait information as well as append to or include location information with the gait information that it receives and uploads to a network-based server, e.g., AS 114. For example, if the gait information is passed from the set of wearable devices 150C via a cellular phone to access network 120, the cellular phone may reveal the GPS location information of the phone. Thus, the GPS location information of the phone can be associated with the contemporaneous gait information of the set of wearable devices 150C. As an alternative, or in addition, each of the base stations 121A and 121B may calculate location information of the device from which it receives the gait information based upon cell tower triangulation, distance and direction estimation and so forth. Thus, when AS 114 and/or AS 114 receives gait information, regardless of whether it is received from local area network 140 or from access network 120, it may include location information and/or time information, in addition to the other parameters such as acceleration, pressure, and so forth obtained by the sensors of a set of wearable devices.

It should be noted that the network 100 has been simplified. For example, the network 100 may include other network elements (not shown) such as border elements, routers, switches, policy servers, security devices, gateways, administrator and user consoles, and so forth.

Figure 2:
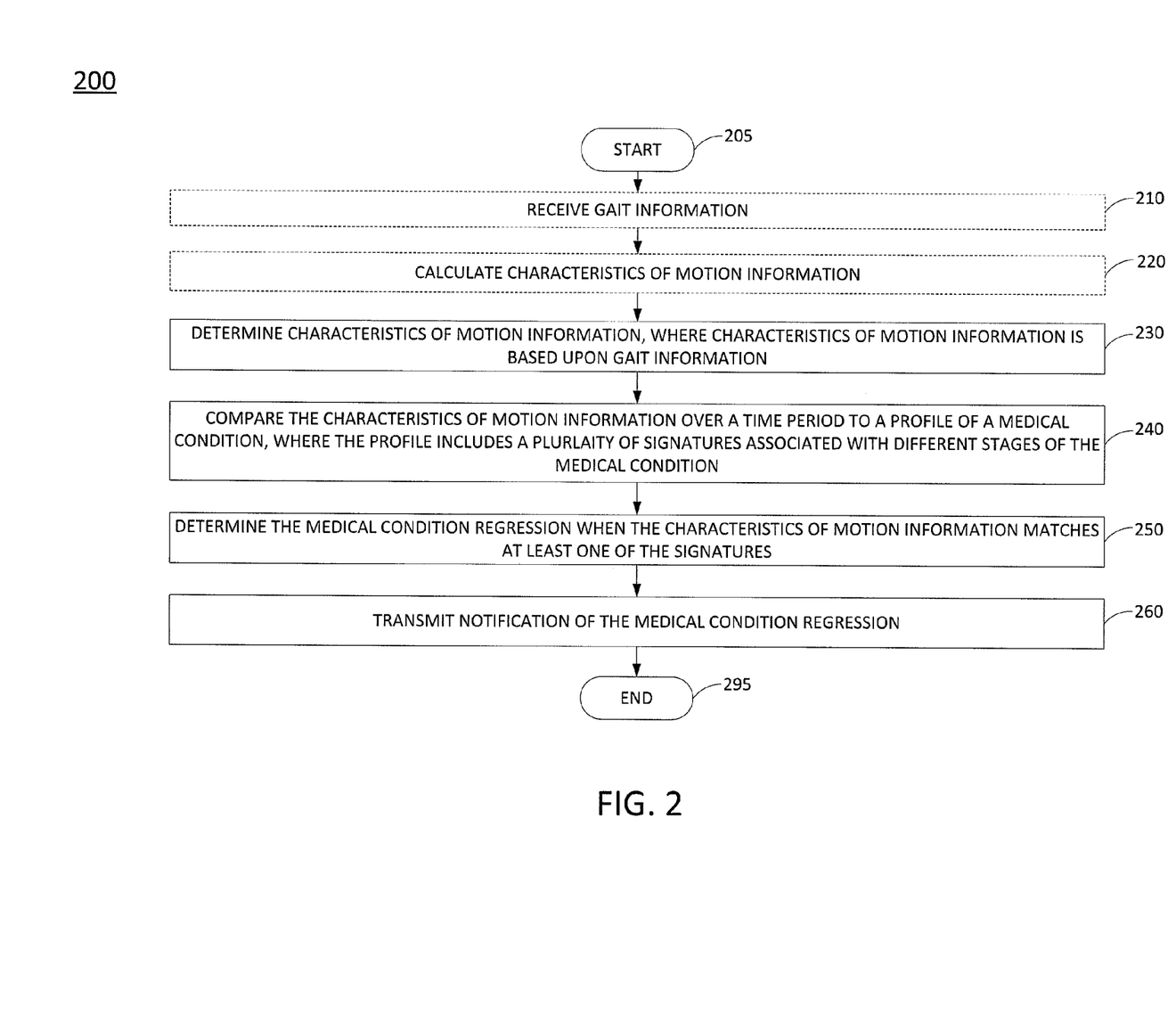
FIG. 2 illustrates an example flowchart of a method for determining a medical condition regression, according to the present disclosure.

FIG. 2 illustrates an example flowchart of one embodiment of a method 200 for determining a medical condition regression, according to the present disclosure. In one embodiment, the method 200 may be performed by an application server such as AS 114 or AS 144 illustrated in FIG. 1. In one embodiment, the steps, functions, or operations of method 200 may be performed by a computing device or system 300, and/or processor 302 as described in connection with FIG. 3 below. For illustrative purpose, the method 200 is described in greater detail below in connection with an embodiment performed by a processor, such as processor 302.

The method 200 begins at step 205 and proceeds to optional step 210. At optional step 210, the processor receives gait information of a user. For example, a set of wearable devices may collect gait information from a number of sensors such as linear accelerometers, gyroscopes, pressure sensors and the like. The processor may receive the gait information from the set of wearable devices via one or more intermediary networks such as a local area network, e.g., a local area network (LAN) that may comprise a ZigBee mesh network, a wired and/or a wireless/cellular access network, and so forth. In one example, the set of wearable devices and/or one or more intermediary components may also append a time stamp and/or location information to the gait information before the gait information is received by the processor.

At optional step 220, the processor calculates characteristics of motion information from the gait information that may be received at step 210. For example, at the previous optional step 210 the processor may receive gait information continuously and/or periodically over a period of time. From the temporal sequence of the gait information, the processor may then determine such motion parameters as a stride length, a speed, an acceleration, an elevation, and so forth, as well as different modes of motion or different types of activities that a user is engaged in at various times within the time period. For example, to determine one or more modes of motion that may be indicated by the gait information, the processor may compare the gait information to known signatures for different common modes of motion/types of activities. In accordance with the present disclosure, at least some of the signatures may relate to movements, stances and/or types of activities associated with one or more regressive medical conditions, and more particularly, the stages of such medical conditions.

At step 230, the processor receives characteristics of motion information that is based upon gait information. For instance, the processor may itself determine the characteristics of motion information, e.g., when performing optional steps 210-220. However, in another embodiment the processor may simply receive the characteristics of motion information from another device. For example, the processor may be a processor of a centralized application server, whereas the functions/operations of steps 210-220 may be performed by another device prior to forwarding the characteristics of motion information to the centralized application server.

At step 240, the processor compares the characteristics of motion information over a time period to a profile of at least one medical condition. For example, as described above a medical condition profile may include a plurality of signatures associated with different stages of the medical condition. In one example, each stage may have multiple different signatures that are associated with the stage. For instance, stage 3 of Parkinson's disease may have signatures for walking, running, standing, and so forth. Stage 4 of Parkinson's disease may have a similar set of signatures, and so forth. Similarly, a profile for Huntington disease may have different sets of signatures relating to early, mid and late stages. Other regressive diseases/medical conditions may have similar profiles and sets of signatures relating to different stages. In any case, various aspects of the characteristics of motion information may be compared to signatures within at least one medical condition profile.

For example, a "walking" signature for stage 3 Parkinson's may reflect that for a certain percentage of the time (e.g., 90% of the time) an average stage 3 user may walk normally, while exhibiting specific instances that are indicative of Parkinson's, such as ankinesia, and bradykinesia, stumbling, falling and the like, for some of the time (e.g., 10% of the time). Similarly, an average stage 4 Parkinson's user may walk normally for 70% of the time and exhibit movements indicative of Parkinson's for 30% of the time, when walking. As such, step 240 may comprise analyzing all the gait information/characteristics of motion information relating to "walking" over a given time period, such as an entire day, to determine a breakdown between normal and impaired walking and then comparing the result to various signatures such as a stage 3 Parkinson's walking signature, a stage 4 Parkinson's walking signature, and so forth. In one embodiment, a similar process may be followed with respect to all of the "jogging" data, all of the stride length data, all of the activity level data, and so forth.

At step 250, the processor determines a potential presence of a regression of a medical condition, e.g., when the characteristics of motion information matches at least one signature. For instance, the processor may determine one or more signatures that are a best match to the observed characteristics of motion information. For example, it may be observed that over the course of a day, or other time period, the user has walked normally for 85% of the time (when walking) and has shown impairment while walking for 15% of the time (when walking). Thus, the processor may determine that Parkinson's stage 3 is a closest, or best match to the observed data. In one embodiment, the determination of a match to a single disease stage signature is sufficient to determine a medical condition regression. However, in another embodiment, at least two signatures from a single disease stage must be matched in order for the processor to determine a medical condition regression has occurred to minimize false positives.

In addition, in a further embodiment, the user may be required to exhibit a change from an earlier determined disease stage to a new disease stage in order to determine that a medical condition regression has occurred. Further examples are described above in connection with the description of AS 114 of FIG. 1. In addition, those skilled in the art will appreciate that other, further and different examples may be devised in accordance with the present disclosure depending upon the particular medical conditions that may be tracked, the particular data points that are available from users, e.g., depending upon the different sensor types that may be deployed for collecting gait information, and so forth.

At step 260, the processor transmits a notification of the medical condition regression when the medical condition regression is determined at step 250. In other words, depending upon the determination at step 250, the processor may notify the user, a medical provider, a caregiver, a physical therapist, etc. In one example, the notification may include various details regarding the determination of the medical condition regression. For example, the notification may include an indication of the particular aspect of the medical condition profile that triggered the determination. For instance, the notification may indicate that the user's gait information matched a signature for stage 3 Parkinson's "walking". The notification may also include additional information such as previous determinations of a user being matched to a disease stage, a current location of a user, an indication of a best matching signature as well as a second best matching signature, and so forth. Such signatures can also be used to record decline of overall physical activity or exertion, which may disclose other medical or psychiatric changes.

Following step 260, the method 200 proceeds to step 295 where the method ends.

It should be noted that although not explicitly specified, one or more steps, operations or blocks of the method 200 described above may include a storing, displaying and/or outputting step as required for a particular application. In other words, any data, records, fields, and/or intermediate results discussed in the methods can be stored, displayed, and/or outputted to another device as required for a particular application. Furthermore, steps, operations or blocks in FIG. 2 that recite a determining operation, or involve a decision, do not necessarily require that both branches of the determining operation be practiced. In other words, one of the branches of the determining operation can be deemed as an optional step. Furthermore, operations, steps or blocks of the above described methods can be combined, separated, and/or performed in a different order from that described above, without departing from the example embodiments of the present disclosure.

FIG. 3 depicts a high-level block diagram of a general-purpose computer suitable for use in performing the functions described herein. As depicted in FIG. 3, the system 300 comprises a hardware processor element 302 (e.g., a central processing unit (CPU), a microprocessor, or a multi-core processor), a memory 304, e.g., random access memory (RAM) and/or read only memory (ROM), a module 305 for determining a medical condition regression, and various input/output devices 306 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the general-purpose computer may employ a plurality of processor elements. Furthermore, although only one general-purpose computer is shown in the figure, if the method(s) as discussed above is implemented in a distributed manner for a particular illustrative example, i.e., the steps of the above method(s) or the entire method(s) are implemented across multiple general-purpose computers, then the general-purpose computer of this figure is intended to represent each of those multiple general-purpose computers.

It should be noted that the present disclosure can be implemented in software and/or in a combination of software and hardware, e.g., using application specific integrated circuits (ASIC), a general purpose computer or any other hardware equivalents, e.g., computer readable instructions pertaining to the method(s) discussed above can be used to configure a hardware processor to perform the steps, functions and/or operations of the above disclosed methods. In one embodiment, instructions and data for the present module or process 305 for determining a medical condition regression (e.g., a software program comprising computer-executable instructions) can be loaded into memory 304 and executed by hardware processor element 302 to implement the steps, functions or operations as discussed above in connection with the exemplary method 200. The processor executing the computer readable or software instructions relating to the above described method(s) can be perceived as a programmed processor or a specialized processor. As such, the present module 305 for determining a medical condition regression (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server. In addition, it should be noted that the hardware processor can be configured or programmed to cause other devices to perform one or more operations as discussed above. In other words, the hardware processor may serve the function of a central controller directing other devices to perform the one or more operations as discussed above.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method for determining a regression of a medical condition, the method comprising:
   receiving, by a processor deployed in a communication network, characteristics of motion information, wherein the characteristics of motion information is based upon gait information;
   comparing, by the processor, the characteristics of motion information over a time period to a profile of the medical condition, wherein the profile of the medical condition comprises a plurality of signatures associated with different stages of the medical condition, wherein each of the plurality of signatures comprises a hidden markov model, wherein each of the plurality of signatures is a signature of a mode of motion that is associated with one of the different stages of the medical condition;
   determining, by the processor, a potential presence of the regression of the medical condition when the characteristics of motion information matches at least two of the plurality of signatures; and
   transmitting, by the processor, a notification of the potential presence of the regression of the medical condition.

2. The method of claim 1, wherein the gait information comprises pressure information.

3. The method of claim 2, wherein the gait information further comprises at least one of: acceleration information or gyroscopic information.

4. The method of claim 1, wherein the transmitting the notification comprises directing an action to be taken.

5. The method of claim 4, wherein the gait information further comprises location information, wherein the action is based upon the location information.

6. The method of claim 1, wherein the characteristics of motion information comprises one of: a stride length, a speed, an acceleration, an elevation, or a mode of motion.

7. The method of claim 1, wherein the medical condition comprises a degenerative disease.

8. The method of claim 7 wherein the degenerative disease comprises one of: Parkinson's disease, Huntington disease, Alzheimer disease, adrenoleukodystrophy, multiple sclerosis, arthritis or dementia.

9. The method of claim 1, wherein the gait information is continuously received and wherein the characteristics of motion information is based upon a temporal sequence of the gait information.

10. The method of claim 1, further comprising:
   receiving the gait information from a set of wearable devices.

11. The method of claim 10, wherein the set of wearable devices comprises a pair of foot-mounted sensors.

12. The method of claim 1, wherein the gait information is received via a network comprising one of: a cellular access network or a ZigBee mesh network.

13. The method of claim 12, wherein a set of wearable devices is for gathering the gait information and for communicating the gait information to one of: the cellular access network or the ZigBee mesh network.

14. The method of claim 13, wherein the set of wearable devices is for communicating the gait information to the ZigBee mesh network when the set of wearable devices is within a communication range of the ZigBee mesh network and wherein the set of wearable devices is for communicating the gait information to the cellular access network when the set of wearable devices is not within the communication range of the ZigBee mesh network.

15. The method of claim 13, wherein the set of wearable devices is for communicating the gait information to the cellular access network via an intermediary cellular endpoint device.

16. The method of claim 1, wherein the gait information is time stamped prior to the gait information being received by the processor.

17. A computer-readable storage device storing instructions which, when executed by a processor deployed in a communication network, cause the processor to perform operations for determining a regression of a medical condition, the operations comprising:
   receiving characteristics of motion information, wherein the characteristics of motion information is based upon gait information;
   comparing the characteristics of motion information over a time period to a profile of the medical condition, wherein the profile of the medical condition comprises a plurality of signatures associated with different stages of the medical condition, wherein each of the plurality of signatures comprises a hidden markov model, wherein each of the plurality of signatures is a signature of a mode of motion that is associated with one of the different stages of the medical condition;
   determining a potential presence of the regression of the medical condition when the characteristics of motion information matches at least two of the plurality of signatures; and
   transmitting a notification of the potential presence of the regression of the medical condition.

18. The computer-readable storage device of claim 17, wherein the gait information comprises pressure information.

19. The computer-readable storage device of claim 18, wherein the gait information further comprises at least one of: acceleration information or gyroscopic information.

20. An apparatus for determining a regression of a medical condition, the apparatus comprising:
   a processor deployed in a communication network; and
   a computer-readable medium storing instructions which, when executed by the processor, cause the processor to perform operations, the operations comprising:
      receiving characteristics of motion information, wherein the characteristics of motion information is based upon gait information;
      comparing the characteristics of motion information over a time period to a profile of the medical condition, wherein the profile of the medical condition comprises a plurality of signatures associated with different stages of the medical condition, wherein each of the plurality of signatures comprises a hidden markov model, wherein each of the plurality of signatures is a signature of a mode of motion that is associated with one of the different stages of the medical condition;
      determining a potential presence of the regression of the medical condition when the characteristics of motion information matches at least two of the plurality of signatures; and
      transmitting a notification of the potential presence of the regression of the medical condition.

* * * * *